United States Patent
Suh et al.

(10) Patent No.: US 9,539,101 B2
(45) Date of Patent: *Jan. 10, 2017

(54) DEVICE FOR STABILIZING A VERTEBRAL JOINT AND METHOD FOR ANTERIOR INSERTION THEREOF

(71) Applicant: GLOBUS MEDICAL, INC., Audubon, PA (US)

(72) Inventors: Sean Suh, Jamesburg, NJ (US); David C. Paul, Phoenixville, PA (US); Jon Suh, Blue Bell, PA (US); Vipin Kunjachan, Jeffersonville, PA (US)

(73) Assignee: GLOBUS MEDICAL, INC., Audubon, PA (US)

( * ) Notice: Subject to any disclaimer, the term of this patent is extended or adjusted under 35 U.S.C. 154(b) by 105 days.

This patent is subject to a terminal disclaimer.

(21) Appl. No.: 14/022,398

(22) Filed: Sep. 10, 2013

(65) Prior Publication Data

US 2015/0073554 A1 Mar. 12, 2015
US 2016/0206438 A9 Jul. 21, 2016

Related U.S. Application Data

(63) Continuation of application No. 12/699,638, filed on Feb. 3, 2010, now Pat. No. 8,350,607.

(51) Int. Cl.
*A61F 2/44* (2006.01)
*A61F 2/30* (2006.01)

(52) U.S. Cl.
CPC ............... *A61F 2/442* (2013.01); *A61F 2/44* (2013.01); *A61F 2/4425* (2013.01); *A61F 2002/304* (2013.01); *A61F 2002/30014* (2013.01); *A61F 2002/30393* (2013.01); *A61F 2002/30405* (2013.01); *A61F 2002/30411* (2013.01); *A61F 2002/30418* (2013.01); *A61F 2002/30517* (2013.01); *A61F 2002/30563* (2013.01); *A61F 2002/30578* (2013.01); *A61F 2002/30599* (2013.01); *A61F 2002/30601* (2013.01); *A61F 2002/30607* (2013.01); *A61F 2002/30616* (2013.01); *A61F 2002/443* (2013.01)

(58) Field of Classification Search
CPC .......... A61F 2/44; A61F 2/442; A61F 2/4425; A61F 2/4455; A61F 2002/443; A61F 2002/4435; A61F 2002/444; A61F 2002/30517
USPC .............................................. 623/17.11–17.16
See application file for complete search history.

(56) References Cited

U.S. PATENT DOCUMENTS

| | | | |
|---|---|---|---|
| 5,888,223 A * | 3/1999 | Bray, Jr. ................. | A61F 2/442 606/247 |
| 6,066,175 A * | 5/2000 | Henderson ................ | A61F 2/44 623/17.11 |
| 6,517,580 B1 | 2/2003 | Ramadan et al. | |
| 6,582,468 B1 | 6/2003 | Gauchet | |

(Continued)

*Primary Examiner* — Eduardo C Robert
*Assistant Examiner* — Marcela I Shirsat

(57) ABSTRACT

A prosthetic device can be used as a prosthesis following a discectomy or a corpectomy. The prosthetic device includes two endplates with staggered motion limiting members. The device can be configured to allow six degrees of motion when comparing one endplate relative to the other. The endplates can be configured to fix the joint by changing the body held within the device and by adding a locking plate and fasteners. A method teaches how to insert a device to an intervertebral space via an anterior incision.

19 Claims, 7 Drawing Sheets

(56) References Cited

U.S. PATENT DOCUMENTS

| | | | |
|---|---|---|---|
| 6,770,095 B2 | 8/2004 | Grinberg et al. | |
| 8,556,974 B2* | 10/2013 | Suh et al. | 623/17.15 |
| 2004/0093082 A1* | 5/2004 | Ferree | 623/17.11 |
| 2004/0127991 A1* | 7/2004 | Ferree | 623/17.11 |
| 2005/0197703 A1* | 9/2005 | Diaz et al. | 623/17.13 |
| 2005/0203626 A1 | 9/2005 | Sears et al. | |
| 2006/0074490 A1 | 4/2006 | Sweeney | |
| 2006/0235518 A1* | 10/2006 | Blain | A61B 17/7059 623/17.11 |
| 2007/0050033 A1 | 3/2007 | Reo et al. | |
| 2007/0282448 A1* | 12/2007 | Abdou | A61F 2/441 623/17.15 |
| 2009/0024218 A1 | 1/2009 | Frigg et al. | |

* cited by examiner

DEVICE FOR STABILIZING A VERTEBRAL JOINT AND METHOD FOR ANTERIOR INSERTION THEREOF

CROSS REFERENCE TO RELATED APPLICATIONS

The present application is a continuation application of U.S. patent application Ser. No. 12/699,638 filed on Feb. 3, 2010, which is incorporated in its entirety herein.

FIELD OF THE INVENTION

The present disclosure generally relates to spinal prostheses and surgical methods for inserting spinal prostheses.

BACKGROUND OF THE INVENTION

The spine includes a series of joints routinely called motion segment units. Motion segment units are the smallest component of the spine that exhibit kinematic behavior characteristic of the entire spine. The motion segment unit is capable of flexion, extension, lateral bending, and translation. The components of each motion segment unit include two adjacent vertebrae and their apophyseal joints, the intervertebral disc, and the connecting ligamentous tissue. Each component of the motion segment unit contributes to the mechanical stability of the joint.

Components of a motion segment that move out of position or become damaged can lead to serious pain and may lead to further injury to other components of the spine. Depending upon the severity of the structural changes that occur, treatment may include fusion, discectomy, or laminectomy.

Underlying causes of structural changes in the motion segment unit leading to instability include trauma, degeneration, aging, disease, surgery, and the like. Thus, rigid stabilization of one or more motion segment units may be an important element of a surgical procedure in certain cases (i.e., injuries, deformities, tumors, etc.), whereas it is a complementary element in others (i.e., fusion performed due to degeneration). The purpose of rigid stabilization is the immobilization of a motion segment unit.

As mentioned above, current surgical techniques typically involve fusing one or more unstable motion segment units and possibly, the removal of ligaments, bone, disc, or combinations thereof included in the unstable motion segment unit or units prior to fusing. There are several disadvantages to fusion, however. For example, the fusing process results in a permanent or rigid internal fixation of all or part of the intervertebral joints and usually involves metallic rods, plates, and the like for stabilization. In all cases, the systems are intended to immobilize rigidly the motion segment unit to promote fusion within that motion segment unit.

In addition to a loss of mobility, fusion also causes the mobility of the motion segment to be transferred to other motion segments of the spine. The added stresses transferred to motion segments neighboring or nearby the fused segment can cause or accelerate degeneration of those segments. One other disadvantage to fusion is that it is an irreversible procedure. In addition, it is believed that fusion of a motion segment has a clinical success of approximately seventy percent (.about.70%), and often does not alleviate pain experienced by the patient.

Analysis of fusion systems going back to the early 1960's has shown that the intentionally rigid designs have often caused stress concentrations and have directly and indirectly contributed to the degeneration of the joints above and below the fusion site (as well as at the fusion site itself). In addition, rigid, linear bar-like elements eliminate the function of the motion segment unit. Finally, removal of portions of the motion segment unit reduces the amount of support available for the affected motion segment unit.

Analysis has also shown that fusion procedures can be improved by modifying the load haring characteristics of the treated spine. Thus, it would be desirable to allow more of a physiologic loading between pedicular fixation and anterior column support. It would also be desirable to have a device that precludes or at least delays the need for fusion for all but the most advanced degeneration of a motion segment, particularly if such a device would allow close to normal motion and pain relief.

SUMMARY

The present application is generally directed to devices and methods for installing a soft spine stabilization system that replicates the physiologic response of a healthy spinal motion segment.

According to one aspect of the invention, a device for stabilizing a first vertebra relative to a second vertebra following discectomies or corpectomies is provided. The device is a prosthesis that is able to articulate in up to six degrees of freedom when installed. In the X-axis, the device allows flexion/extension and lateral slip. In the Y-axis, the device allows a joint to have left/right axial rotation and anterior/posterior slip. In the Z-axis, the device allows left/right lateral bending. The device includes a superior endplate with at least one motion limiting member and inferior endplate with at least one motion limiting member. A body is held between the endplates. The motion limiting member on the superior endplate extends inferiorly (i.e. downward) below the inferior surface of the endplate. The motion limiting member of the inferior endplate extends superiorly (i.e. above) the superior surface of the inferior endplate. The body is disposed between the endplates and is held, at least in part, within the device by the motion limiting members. The motion limiting member of the superior endplate contacts the motion limiting member of the inferior endplate to limit motion of the endplates relative to each other.

The endplates may generally have a transverse section shaped like the abutting (i.e. superior or inferior) surface of the body of the vertebra being supported. Generally, this shape is a trapezoid shape. The longer base on the trapezoid is on the anterior side of the vertebra. The shape of the endplate is said to be "generally" trapezoid shaped because the shape can be curvilinear to compliment the anatomy being supported.

The motion limiting members may have a generally rectangular cuboid shape. The edges of the motion limiting members can be rounded.

According to a further aspect of the invention, the motion limiting members on the superior endplate are staggered with respect to the motion limiting members on the inferior endplate. "Staggered" generally means that the motion limiting members alternate between a motion limiting member disposed on the superior endplate and a motion limiting member disposed on the inferior endplate. In addition, "staggered" connotes that there can be at least some separation between a motion liming member and a neighboring motion liming member.

By being staggered, the motion limiting members on the superior endplate can enmesh with the motion limiting members on the inferior endplate. In addition, by being staggered and enmeshed the motion limiting members can move in a limited amount relative to each other until they contact each other. The staggered positioning allows the six degrees of freedom discussed previously while simultaneously can limit the amount of freedom in those degrees of freedom.

According to a further aspect of the invention, the body has a height, and the motion limiting members on the endplates are generally shorter than the body. By being shorter than the body, the body may still compress by the difference in heights before a motion limiting member on an opposing endplate contacts the opposing endplate. In general, such a feature minimizes wear from rubbing between the endplate and the opposing motion limiting member. It also limits movements and prevents the body from being compressed to an extreme thinness.

According to a further aspect of the invention, a motion limiting member on the superior endplate is disposed on the same side of the body as a motion limiting member on the inferior endplate. By having a motion limiting member on the superior endplate and the inferior endplate, the body is secured on the given side by the motion limiting members and cannot slip from the superior endplate and the inferior endplate. Additional pairs (i.e. a superior and an inferior) of motion limiting members can be disposed about a periphery of the endplates to secure the body between the endplates.

According to a further aspect of the invention, motion limiting members can be disposed on a given endplate on opposite sides of the body. For example, an endplate can have an anterior motion limiting device and a posterior motion limiting device. In this way, the body can be secured between the two motion limiting devices. The motion limiting members that are disposed on opposite sides of the body also can be placed with one on each of the endplates. Combinations of motion limiting members can be added to secure the body between the endplates and to provide the proper restrictions on the range of motion of the joint.

According to a further aspect of the invention, the endplate can have at least one bore to promote bone growth therethrough. The bore can be a single large bore. Alternative, a plurality of smaller bores can be formed in each endplate. Bone will generally grow into the bore and help to secure the prosthesis to the adjacent vertebra.

According to a further aspect of the invention, screw anchoring members can be added to the superior surface and the inferior surface to fasten the device to the vertebrae. While each endplate can be secured to a respective vertebra, it is possible for only one screw anchoring member to be used. The screw anchoring member is a tab with a socket formed therein. The socket can be threaded or unthreaded. The screw anchoring member can be disposed on the anterior edge of a respective endplate. By being on the anterior edge, the device can be slid into position from an anterior position to place the screw anchoring members in contact with the vertebra. The screw anchoring members can be configured to be vertically aligned with movement limiting members on the anterior edge. A fastener is used to attach the screw anchoring member to the vertebra. A bone screw is one preferred form of fastener. Other fasteners such as sutures, staples, and nails can be used.

The device can include a locking plate for fixing one vertebra relative to another vertebra. The locking plate can be installed on an anterior of the vertebrae in a spinal joint. The locking plate has a first screw anchoring member and a second screw anchoring member. Each screw anchoring member receives a respective fastener that connects to a respective vertebra. The first screw anchoring member is configured to connect to a first vertebra. The second screw anchoring member is configured to connect to a second vertebra. The locking plate can be screwed into a vertebra or vertebrae that is/are immediately adjacent to the rest of the device. The locking member can overly the superior endplate and the inferior endplate. When the locking plate is installed, the two vertebrae are fixed in position relative to each other. Typically, the fastener is a bone screw.

The locking member can be configured so that the anchoring member extends beyond an endplate at a position that is vertically aligned with a motion limiting member on the opposing endplate. For example, the superior screw anchoring member of the locking plate can be configured to connect to a vertebra, above a motion limiting member on the inferior endplate. Likewise, the inferior screw anchoring member of the locking plate can be configured to connect to a vertebra below the motion limiting member of the superior endplate.

The screw anchor members of the locking plate can be configured to connect to a vertebra alongside the screw anchor member of respective endplates. The screw anchor members can press against each other and even contact each other. By pressing against each other, the locking plate forms a particularly stiff, reinforced fixed joint. In the case of abutting screw anchor members, a contact surface is defined where the two abut.

The device including the body, the superior endplate, and the inferior endplate can have a combined height substantially equal to an intervertebral disc that is to be replaced. By having a height substantially equal to a disc, the device can be used as a prosthesis in a discectomy. The device is said to be "substantially" equal to the height of the disc because the original disc might be compressed or damaged. Accordingly, the height of the device should be the size that is desired.

The device including the body, the superior endplate, and the inferior endplate can have a combined height substantially equal to a vertebra and attached superior and inferior intervertebral discs that are to be replaced. By having a height substantially equal to a vertebra and adjacent discs, the device can be used as a prosthesis in a corpectomy. The device is said to be "substantially" equal to the height of the vertebra because the original vertebra and/or discs might be compressed or damaged. Accordingly, the height of the device should be the height that is desired.

The body held between the endplates can be flexible and resilient. By being flexible, the body can move and compress to allow movement of one endplate relative to the other endplate. When the body is resilient, the body tends to return to its original state after being moved or compressed.

The body can have a fixed height. The body can be rigid. A body with a fixed height is useful when the joint is to be fixed.

The body can be made of different materials to affect its qualities, in particular its flexibility. The body can be made of a single homogenous material. The body can have layers of different materials to control the physical properties of the body. The materials in the different layers can have different properties.

The body can be a self-standing single body cage. U.S. Pat. No. 7,137,997 is incorporated by reference as an example of a self-standing single body cage.

The body of the device can be a self-standing expandable cage. U.S. Pat. Nos. 7,384,431, 5,702,453, and 5,236,460 are incorporated by reference as examples of self-standing expandable cages.

A fastener can be inserted through the body and into a vertebra to stabilize being connected to said body and configured to insert into a vertebra. The fastener can fix and stabilize the body relative to the vertebra.

The device according to the invention can have a motion limiting member on each side (anterior, posterior, left, and right) of each endplate. The body is placed between the motion limiting members. The motion limiting member prevents the body from moving laterally from between the endplates. The body limits how far one end plate can shift relative to the other when there are surrounding motion limiting members.

The motion limiting members disposed on the superior endplate can be staggered with regard to the motion limiting members disposed on the inferior endplate. "Staggered" is generally meant to mean that the motion limiting members are offset from each other with reference to vertical alignment. In other words, a motion limiting member on the top does not align vertically with a motion limiting member on the top. In addition, a gap can be left between adjacent superior and inferior motion limiting members. The gap in the staggered motion limiting members allows for a desired amount of play to allow for freedom of movement of one endplate relative to another. The amount of play can be controlled by adjusting the width of the gaps. By being staggered, the motion limiting members on the superior endplate can enmesh with the motion limiting members on the inferior endplate.

The device, in particular the endplates, can be made from a biocompatible material. Examples of biocompatible material include biocompatible metals and biocompatible polymers.

The outer surface (i.e. superior surface on the superior endplate or the inferior surface on the inferior endplate) of each end plate can be configured to support an adjacent vertebra. The outer surface of each endplate can be textured with devices to increase friction between the endplate and the adjacent vertebrae. The devices to increase friction can be pyramid or tetrahedron shaped spikes.

The invention may also include a method of stabilizing a superior vertebra with respect to an inferior vertebra following a discectomy or corpectomy. The method includes forming an incision to anterior of an intervertebral space. The intervertebral space at least originally has an intervertebral disc; the intervertebral disc may have been replaced by a prosthesis in a previous procedure. A superior vertebra is disposed superior to the intervertebral disc. An inferior vertebra is disposed inferior to the intervertebral disc. The superior vertebra and the inferior vertebra each have an anterior face.

In the next step, a device as described previously is inserted anteriorly via the anterior incision into the intervertebral space. The device is inserted from the anterior until the superior screw anchoring member contacts the anterior face of the superior screw anchor member. The inferior anchoring member also should be contacting the anterior face of the inferior screw anchor member. The next step includes fastening the first screw anchoring member to the anterior face of said superior vertebra. Usually, the fastening step is accomplished by a inserting a bone screw through the screw anchoring member into the vertebra. Likewise, the method includes fastening the second screw anchoring member to the anterior face of the inferior vertebra. The fastening can be accomplished by screwing a bone screw through the anchoring member into the vertebra.

The invention encompasses a method of stabilizing a superior vertebra with respect to an inferior vertebra following a discectomy or corpectomy. The method can begin with forming an incision to anterior of an intervertebral space having a superior vertebra with an anterior face. In the next step, a device as described previously is inserted via the anterior incision to the intervertebral space. The next step includes fastening a first screw member to the anterior face of a superior or an inferior vertebra. The next step can include fastening the second screw member to the anterior face of the other vertebra.

The method of securing the vertebrae to each other can include adding a locking plate, which has been described previously. The locking body is placed over the device. The locking body can be placed to overly the superior endplate and the inferior endplate. The locking plate can be configured to abut the screw anchor members. The locking body is then fastened to the superior vertebra and the inferior vertebra.

Other features that are considered as characteristic for the invention are set forth in the appended claims.

Although the invention is illustrated and described herein as embodied in a device for stabilizing a vertebral joint and a method for anterior insertion of the device, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE ILLUSTRATED EMBODIMENTS

Figure 15:
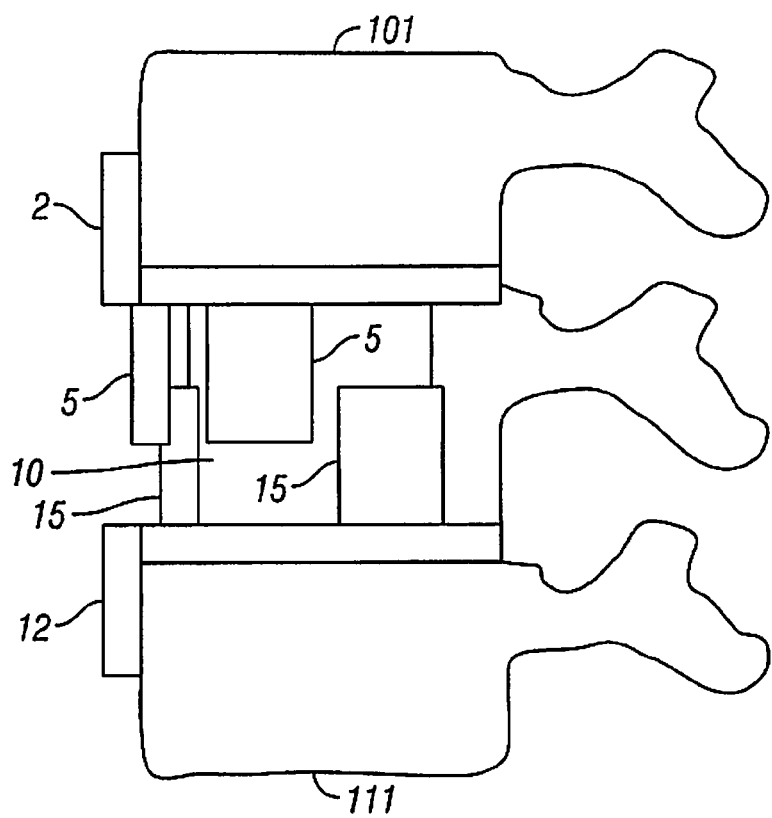
FIG. 15 is a left side view of a device being inserted anteriorly in a corpectomy.
Figure 16:
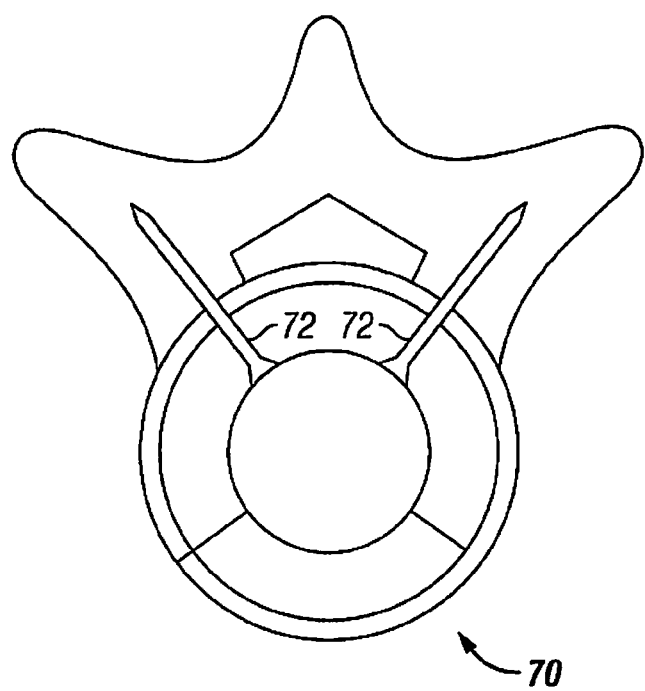
FIG. 16 is a top side view of the device shown in FIG. 15 installed after a corpectomy.

Referring now to the figures of the drawing in detail and first, particularly, to FIGS. 1-6 thereof, there is seen a device 20 for stabilizing a first bone of a joint relative to a second bone of a joint. In particular, the device 20 is useful for stabilizing a first vertebra relative to a second vertebra following discectomies or corpectomies. The device 20 includes a superior endplate 1 and inferior endplate 11. As shown in FIG. 15, the superior endplate 1 is configured to support a superior vertebra 101. The inferior endplate 11 is configured to support an inferior vertebra 111. In one embodiment, a superior surface 8 of the superior endplate 1 is textured to increase friction between the superior vertebra 101 and the superior endplate 1. Likewise, the inferior surface 18 of the inferior endplate 11 is textured. The textured surface can include teeth, ridges, and/or grooves. These protrusions extend from a bone engaging surface of the device and engage bone of the joint to reduce or prevent movement of the surface relative to the bone. The superior surface 8 and inferior surface 18 either directly contact the superior vertebra 101 or inferior vertebra 111, respectively, or intervening layers and bodies, which are not shown, can be inserted therebetween.

Figure 1:
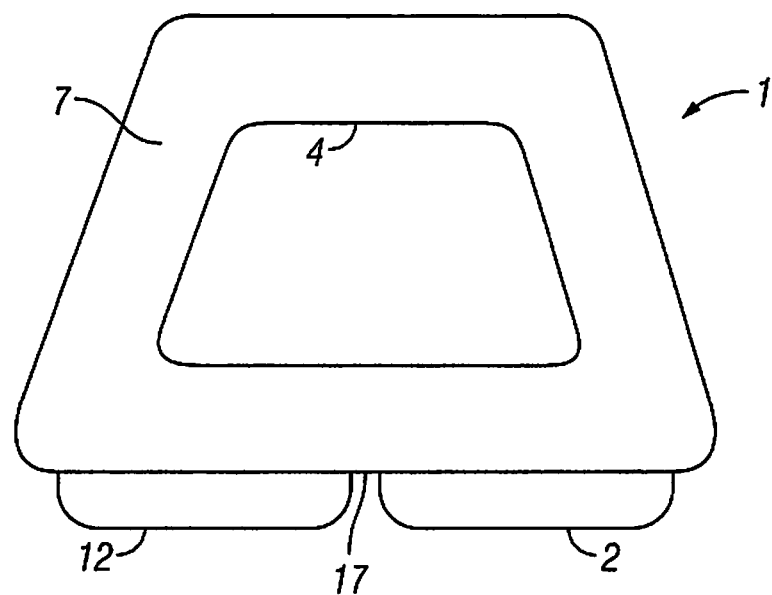
FIG. 1 is a diagrammatic top side view of a device according to the invention.

In the embodiment shown in FIG. 1, the superior endplate 1 has a bone growth bore 4 formed therein. Multiple bores 4 are formed in the embodiment of the inferior endplate shown in FIG. 6. Bone tissue from an adjacent bone can grow into bone growth bore 4. Growing bone into the bone growth bore 4 forms a strong connection between the bone and the device 20.

Figure 6:
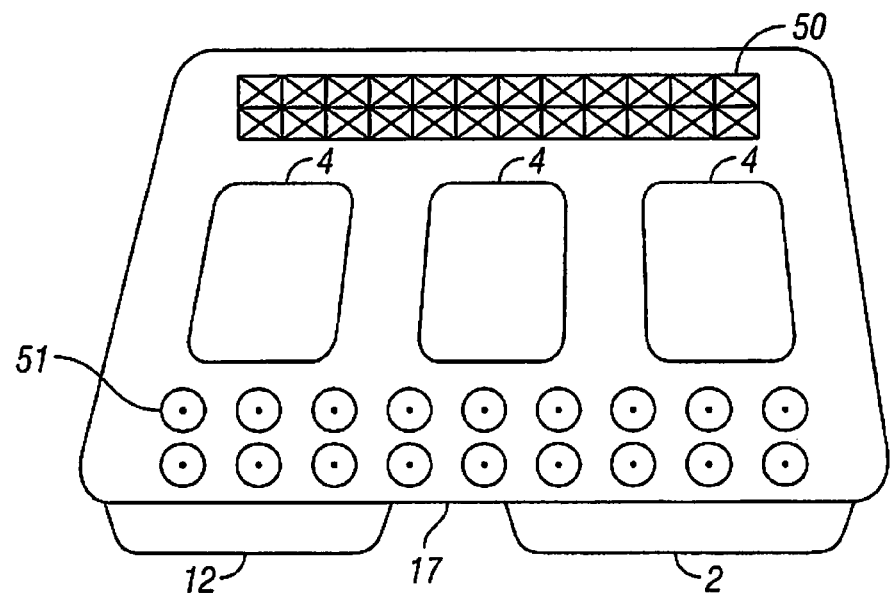
FIG. 6 is a bottom side view of the device shown in FIG. 1.

As shown in FIGS. 1 and 6, the endplates 1 and 11 have a cross section that is similar to the cross section of the vertebrae being supported. Generally, this shape is substantially trapezoidal. With respect to the shape, "substantially" means that the shape is interpreted as generally trapezoidal but the sides may be curvilinear. The larger base of the trapezoid shape is to be the anterior edge (i.e. front edge).

Motion limiting members 5 extend downward (i.e. inferiorly) from the superior endplate 1. The motion limiting members 5 are spaced apart from each other. In the preferred embodiment, the motion limiting members are rectangular cuboids. The edges can be rounded.

Motion limiting members 15 extend upward (i.e. superiorly) from the inferior endplate 11. The motion limiting members 15 are spaced apart from each other. In the preferred embodiments, the motion limiting elements 15 are rectangular cuboids. The edges can be rounded.

When the endplate 1 and the endplate 11 are brought together, the motion limiting members 5 and 15 seat between each other. Space can remain between the motion limiting members 5 and 15 to allow the endplates 1 and 11 to move relative to each other. The relative movement is subject to the compressive and elastic qualities of a body 10; the body 10 is described in detail below. However, when the endplates 1 and 11 move too far laterally from each other, a given motion limiting members 5 and 15 contact a neighboring motion limiting member 5 or 15 to limit how far the endplates 1 and 11 can shift relative to each other. The amount of lateral movement allowed can match a typical range of motion before the implantation or can match an amount that the device 20 is safe to allow. In the preferred embodiment, the motion limiting members 5 and 15 alternate between a motion limiting member 5 on the superior endplate 1 and a motion limiting member 15 on the inferior endplate 11.

The motion limiting members 5 and 15 are distributed about the perimeter of the respective endplate 5 and 15. In an exemplary embodiment, a motion limiting member 5 is located at each corner of the superior endplate 1. A motion limiting member 15 is located in the middle of each edge of the inferior endplate 11.

A body 10 is placed between the superior endplate 1 and the inferior endplate 11. The body 10 is placed in the center in the middle of the motion limiting members 5 and 15, which are disposed about the perimeter of the endplates 1 and 11. Embodiments of the body 10 are discussed later in the specification. The body 10 has a height that is sized so that the overall height of the device (i.e. the height of the endplates 1 and 11 plus the height of the body 10) is substantially equal to the space in which the device is being inserted. For example, if the device were to replace an intervertebral disc, the height of the device would be equal to the height of the intervertebral disc. If the device were replacing a vertebra, the height of the device when installed would be equal to the height of the vertebra. The combined height is said to be "substantially" equal because often the anatomy being replaced has degenerated and is compressed so the height of the replacement may be slightly larger to provide a replacement of what the height should be.

In one embodiment, the motion limiting members 5 and 15 have a height from the face of the endplate that is less than the height of the body 10. In this way, the body 10 can compress axially and the motion limiting members 5 and 15 will not contact the opposing endplate.

In the preferred embodiment, the motion limiting members 5 and 15 have a height at least as high as the expected amount of axial expansion. In this way, the motion limiting members 5 and 15 will remain in contact with the body 10 even when the spine is at its greatest length. Accordingly, the motion limiting members 5 and 15 never become disengaged from the body 10.

The space between a given limiting member 5 or 15 with neighboring motion limiting members 15 or 5, respectively, should be great enough to allow the intended range of motion. The space between should not be so great to exceed a safe amount of twisting.

A screw anchor member 4 extends superiorly (i.e. upward) from the superior endplate 1. The screw anchor member 4 is a rectangular tab, although other shapes are possible. The screw anchor member 2 extends upward from an anterior edge 7 of the endplate 1. The screw anchor member 2 is disposed above the motion limiting member 5 on the anterior edge 7. A socket 3 is formed in the screw anchor member 2. The socket 3 is preferably threaded and counter sunk. In an alternate embodiment, the socket 3 is not threaded and not counter sunk. A bone screw 30 is screwed though the socket 3 into the underlying body of the vertebra.

The bone screw 30 includes a head 31. The head 31 cannot pass through the socket 3. The head and socket 3 may be polyaxially matable to facilitate secure attachment of the screw to bone, for example, cortical bone. The head 31 has a socket 32 formed therein. The bone screw includes a thread 33.

A screw anchor member 14 extends inferiorly (i.e. downward) from the inferior endplate 11. The screw anchor member 14 is a rectangular tab. The screw anchor member 12 extends downward from an anterior edge 17 of the endplate 11. The screw anchor member 12 is disposed below the motion limiting member 15 on the anterior edge 17. A socket 13 is formed in the screw anchor member 12. The socket 13 is preferably threaded and counter sunk. In an alternate embodiment, the socket 13 is not threaded and not counter sunk. A bone screw 30 or compatible fastener is screwed though the socket 3 into the underlying body of the vertebra.

In the preferred embodiment, the device 20 allows six degrees of motion in the joint. In the X-axis, the device 20 allows flexion/extension and lateral slip. In the Y-axis, the device 20 allows left/right axial rotation and anterior/posterior slip. In the Z-axis, the device 20 allows left/right lateral bending and axial tension/compression.

Figure 7:
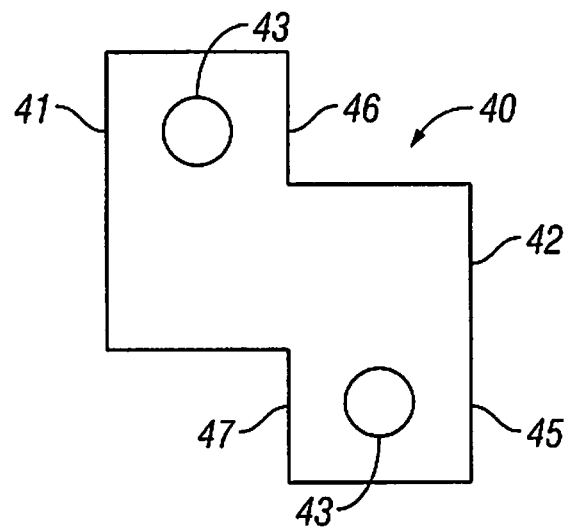
FIG. 7 is a front side view of a locking plate according to the invention.
Figure 8:
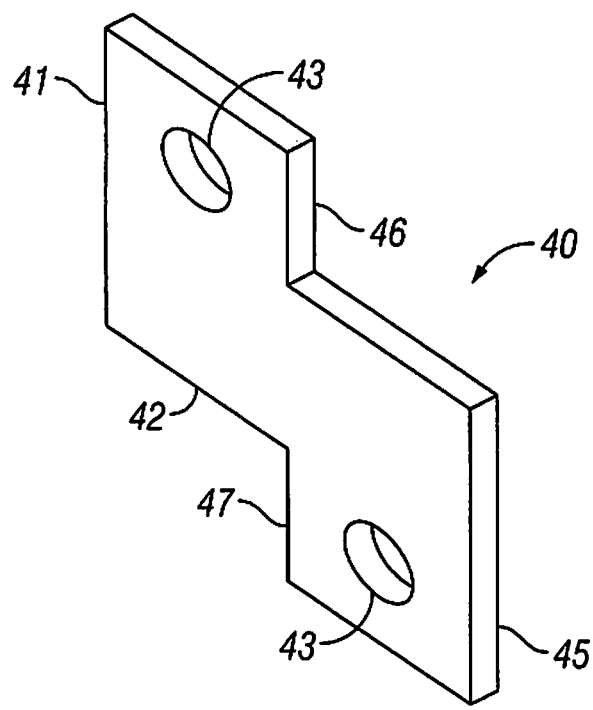
FIG. 8 is a perspective view of the locking plate shown in FIG. 7.
Figure 9:
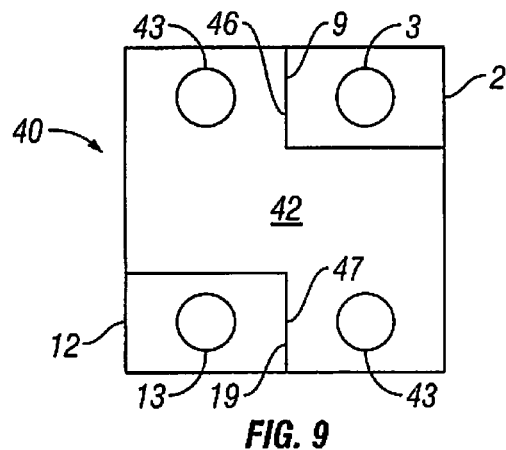
FIG. 9 is a front side view of the device shown in FIG. 2 with the locking plate shown in FIG. 7 installed.
Figure 10:
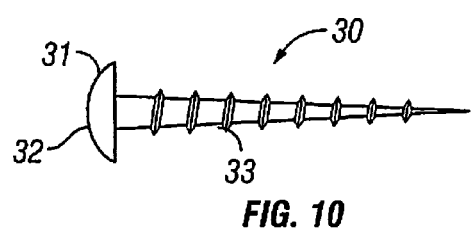
FIG. 10 is a perspective view of a screw according to the invention.

FIGS. 7-9 show a preferred embodiment of locking plate 40. The locking plate 40 has a horizontal plate 42. A superior screw anchoring member extends superiorly (i.e. upwardly) from said horizontal plate 42. The superior screw anchoring member 41 is a rectangular tab. The superior screw anchoring member 41 has a socket 43 formed therein. The socket 43 is threaded and countersunk. An inferior screw anchoring member 45 extends inferiorly (i.e. downwardly) from said horizontal plate 42. The inferior screw anchoring member 45 may also have a socket 43 formed therein. The socket 43 is threaded and countersunk. In other embodiments, the socket is unthreaded or not countersunk. The locking plate 40 is configured to be tall enough so that the superior screw anchoring member 41 overlies a superior vertebra while the inferior screw anchoring member 45 overlies an inferior vertebra. Screws 30 are screwed into each screw anchoring member 41 and 45 and underlying bone to fasten the locking member 40 to the vertebrae. When installed, the vertebrae are no longer able to move relative to each other.

The locking plate 40 is placed over the anterior face of the device 20. The horizontal plate 42 overlies the superior endplate 1 and the inferior endplate 11. The superior screw anchoring member 41 of the locking plate 40 is adjacent the superior screw anchoring member 12 of the superior endplate 1. The inferior anchoring member 45 of the locking plate 40 is adjacent the superior screw anchoring member 22 of the inferior endplate 11. The superior anchoring member 41 of the locking plate 40 is inline vertically with the inferior anchoring member 12 of the inferior endplate 11. The inferior anchoring member 41 of the locking plate 40 is inline vertically with the superior anchoring member 2 of the superior endplate 1.

The screw anchoring members 41 and 45 of the locking plate 40 abut the screw anchoring members 2 and 12 of the endplates 1 and 11. Each of the screw anchoring members 41 and 45 has a medial contact surface 46 and 47, respectively. The screw anchoring member 2 has a medial contact surface 9. The screw anchoring member 12 has a medial contact surface 19. When the locking plate 40 is installed, the contact surface 46 abuts the contact surface 9 and the contact surface 47 abuts the contact surface 19. While it is preferred that the contact surfaces directly contact each other, intervening objects can be placed between them.

The device 20 and locking plate 40 are made of a biocompatible material. Preferably, the device 20 and locking plate 40 are made of a biocompatible metal or polymer.

Figure 2:
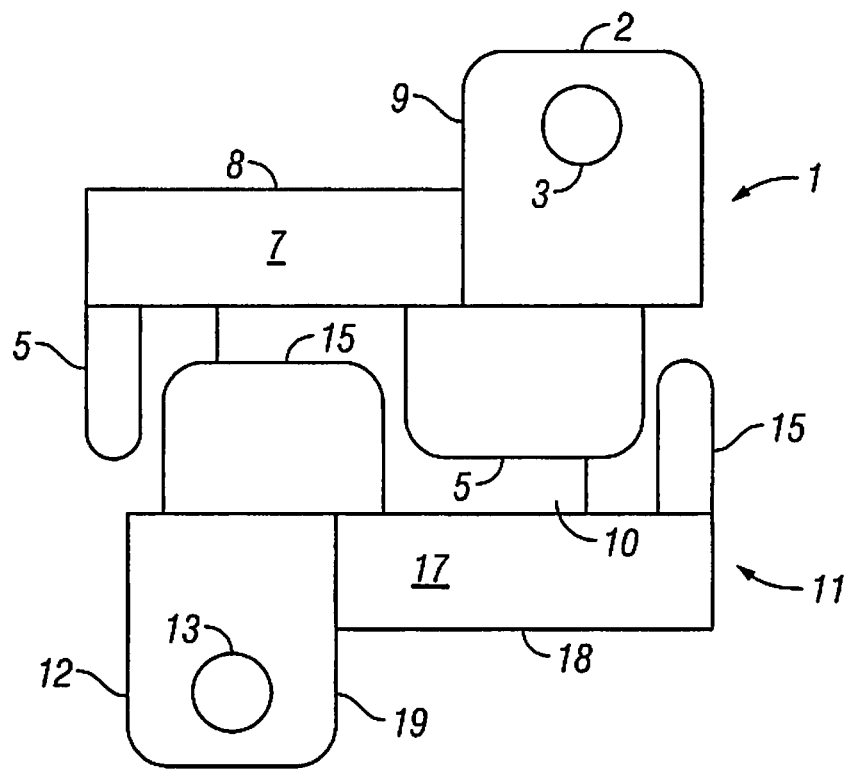
FIG. 2 is a front side view of the device shown in FIG. 1.
Figure 3:
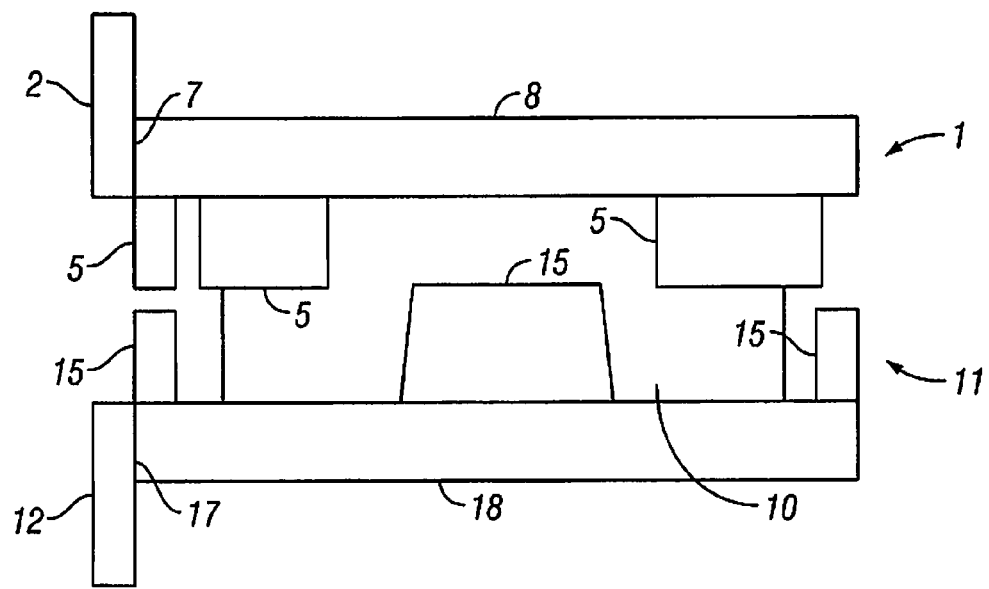
FIG. 3 is a left side view of the device shown in FIG. 1.
Figure 4:
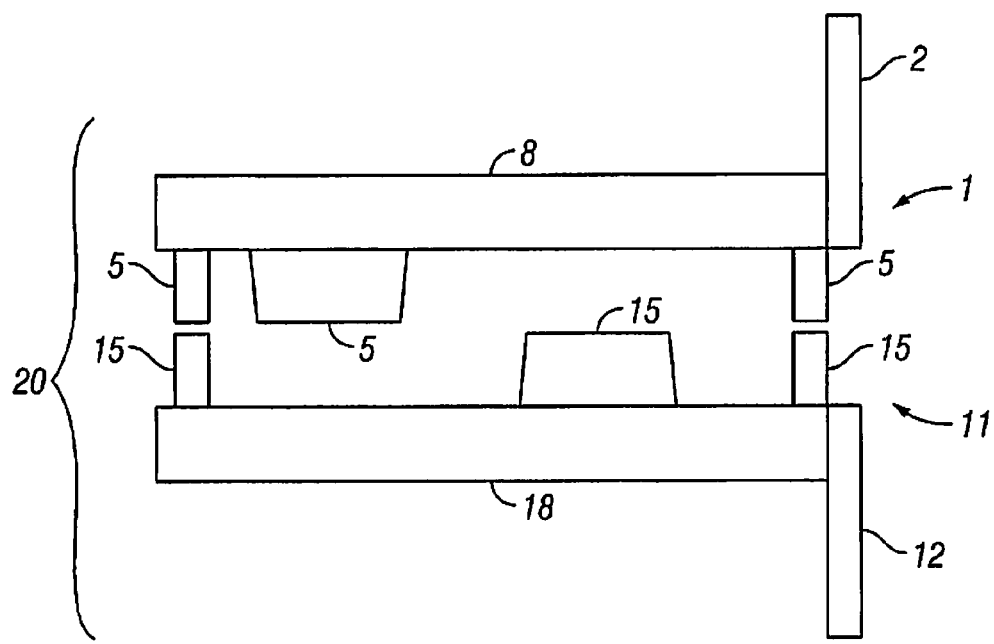
FIG. 4 is a right side view of the device shown in FIG. 1.
Figure 5:
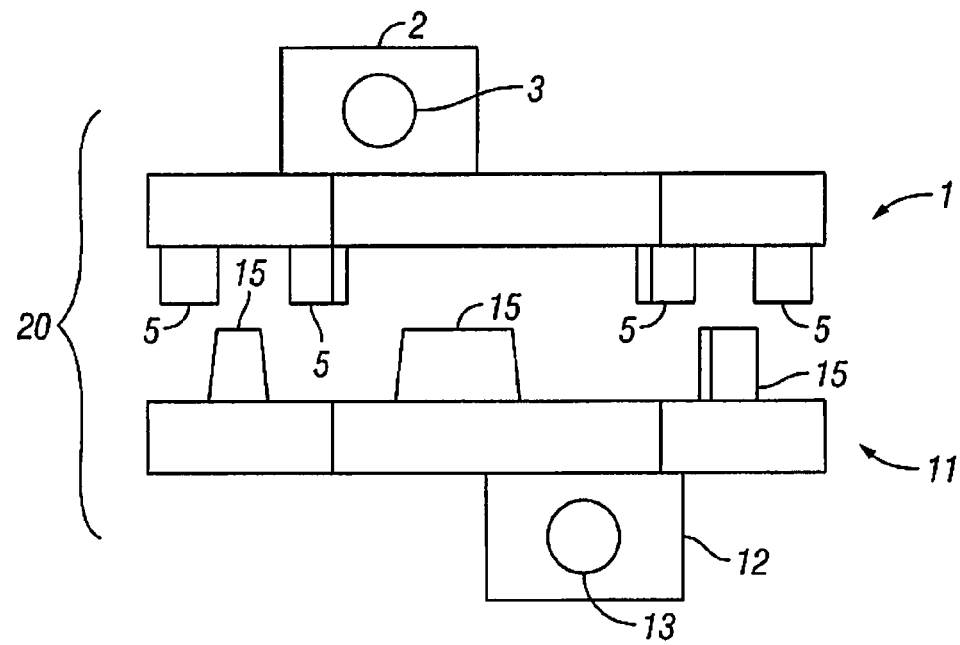
FIG. 5 is a rear side view of the device shown in FIG. 1.

In one embodiment shown in FIGS. 2-4, the device 20 allows for movement. In this embodiment, the body 10 is flexible and resilient. A suitable material allows for temporary motion of the endplate 1 relative to the endplate 11 and then helps to return the endplates 1 and 11 to their original position. The body 10 is sandwiched between the superior endplate 1 and the inferior endplate 11. The body 10 is surrounded by and retained by the motion limiting members 5 and 15. The body 10 is compressible and flexible to allow one endplate 1 to move relative to the other endplate 11. As the body 10 compresses and flexes, the motion limiting members 5 of the superior endplate 1 intermesh with the motion limiting members 15 of the inferior endplate 11.

Figure 11:
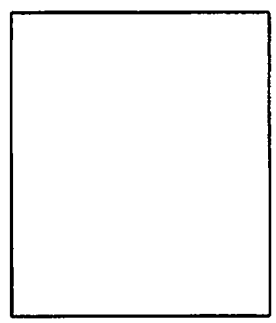
FIG. 11 is a side view of a first embodiment of a body that is homogeneous.
Figure 12:
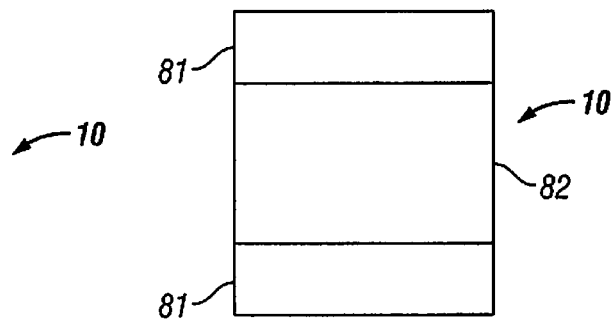
FIG. 12 is a side view of a second embodiment of a body having three layers.

In the embodiment shown in FIG. 11, the body 10 is made of a single material and is homogeneous. In the embodiment shown in FIG. 12, the body 10 is made of different materials. The body 10 has three layers 61 and 62. The outer layers 61 are made of a first material. The inner layer 62 is made of a second material. The first material has different mechanical properties (i.e. flexibility, resiliency, durability, etc.) than the second material. The material or materials of the body 10 are selected to match a desired flexibility of the device 20. The body 10 can be made to flex like the original anatomy or within the mechanical limits of the device 20.

Figure 14:
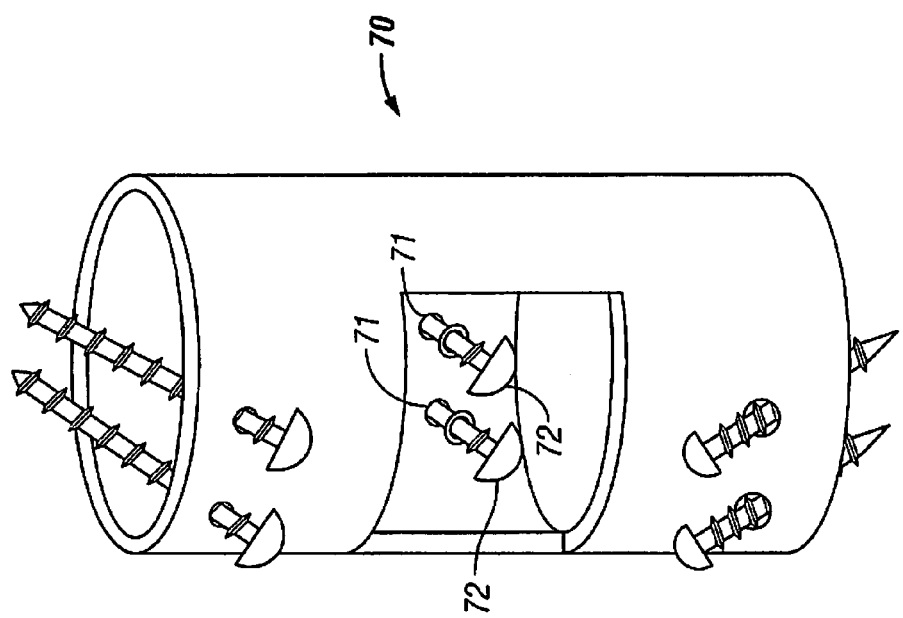
FIG. 14 is a perspective view of a self-standing single body cage.
Figure 13:
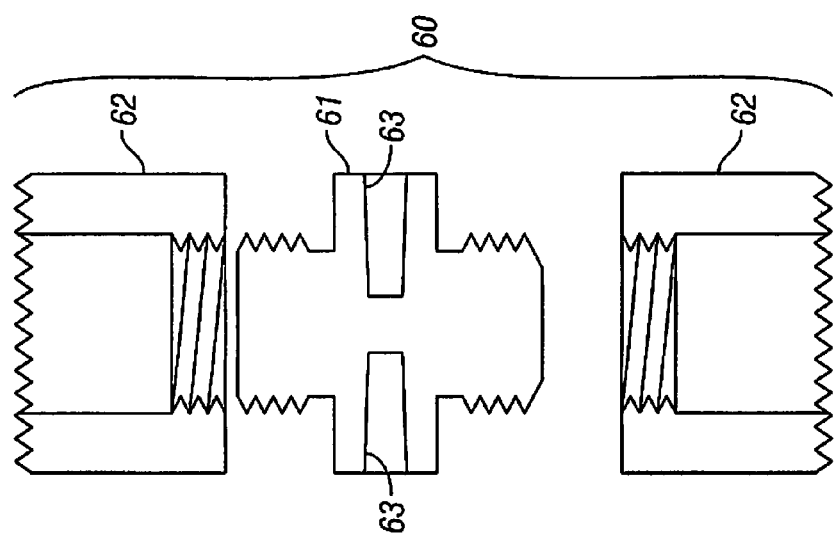
FIG. 13 is a perspective view of a self-standing expanding cage.

In the embodiments shown in FIGS. 13 and 14, a fixed bone spacer is used as the core. The fixed bone spacer is not flexible. Accordingly, the endplates 1 and 11 do not move relative to each other when the fixed bone spacer is used as the body 10. FIG. 13 shows an embodiment with a standing expanding cage as the core. An example of a standing expandable cage is taught in U.S. Pat. No. 7,384,431, which is incorporated by reference herein. FIG. 14 shows an embodiment in which a standing single body cage is used as the body 10. Screws 30 are inserted through the body 10 into the pedicle of the vertebra to fix the body to the vertebra. The device 20 provides a device that can be used for an anterior installation with greater stability than an expanding cage alone.

A preferred embodiment of the invention includes a method of stabilizing a first vertebra relative to a second vertebra after a discectomy. An incision is made to an anterior aspect of an intervertebral disc of the spine. Next, the intervertebral disc is removed via the anterior incision. If a prosthesis had been inserted previously to replace an intervertebral disc, the prosthesis can be removed via the incision. Next, the device is inserted into the intervertebral space from which the disc was removed. The joint can be expanded or the device compressed to help insert the device 20 into the intervertebral space. To compress the device 20, the superior endplate 1 can be pressed toward the inferior endplate 11 to compress the body 10. When inserting the device 20, the anterior edge 117 is aligned along the anterior of the spine. When the device 20 is inserted, the superior surface 8 of the superior endplate 1 presses against the superior vertebra. Likewise, the inferior surface 18 of the inferior endplate presses against the inferior vertebra. To fix the device 20 to the vertebra, a screw is inserted through the socket 3 of the screw anchor member 2 into the anterior face of the body of the superior vertebra. Likewise, a screw 30 is inserted through the socket 13 of the screw anchor member 12 into the anterior face of the body of the inferior vertebra. Next, the incision is closed.

When the superior endplate 1 is connected to the superior vertebra and the inferior endplate 11 is connected to the inferior vertebra, the device 20 preserves movement along six degrees of freedom: X-axis: flexion/extension, lateral slip; Y-axis: Left/Right Axial Rotation; Anterior/Posterior Slip; Z-Axis: Left/Right Lateral Bending, Axial tension/compression. A practitioner can determine a permissible range of motion by configuring the body 10 and the spacing and size of the motion limiting members 5 and 15.

A preferred embodiment of a method for providing soft stabilization utilizes a locking plate 40. The device 20 is installed as described previously. Next, a locking plate 40 is placed over the device 20. The horizontal plate 42 is placed to overly the endplates 1 and 11. The superior screw anchor member 41 is placed on the anterior face of the superior vertebra. The superior screw anchor member 41 is aligned vertically above the anterior motion limiting member 15 on the inferior endplate 11. The superior screw anchor member 41 is placed so a medial contact surface 46 abuts a medial contact surface 9 of the superior screw anchor member 2 of the superior endplate 1. Likewise, the inferior screw anchor member 45 is placed so its medial contact surface 47 abuts a medial contact surface 19 of the inferior screw anchor member 12 of the inferior endplate 11. The locking plate 40 limits the motion of the first endplate 1 with respect to the second endplate 11. However, depending on the qualities of the body 10, some motion still may be provided even when the locking plate 40 is installed.

A preferred embodiment of a method for stabilizing a vertebra with respect to another vertebra following a corpectomy utilizes the device 20. An incision is made to an anterior surface of a vertebra. The body of the vertebra is removed during the corpectomy. The device 20 is delivered to the site where the body of the vertebra was removed via the anterior incision. In the preferred embodiment, the body 10 is not flexible and has a height so the overall height of the device 20 including the superior endplate 1, body 10, and inferior endplate 11 is substantially equal to the height of the vertebra being replaced. "Substantially" is used to denote that the height may not be exactly the same as the vertebra being replaced. For example, if the vertebra being replaced was damaged, or compressed, the device 20 might need a height slightly greater or less than the vertebra being replaced. The body 10 can be a rigid homogenous piece of material or have layers of different stiffness. In a preferred embodiment, the body 10 is a self-standing expanding cage. The expanding cage is operated to adjust a height of the self-standing expanding cage to match the height of the vertebra being replaced. In another embodiment, the body 10 is a self-standing single body cage. Screws are inserted from an anterior side into the pedicle of the vertebrae that has had its body removed. In one embodiment, the body 10 is fastened to each of the superior endplate 1 and inferior endplate 11 with respective screws 30.

While it is apparent that the invention disclosed herein is well calculated to fulfill the objects stated above, it will be appreciated that numerous modifications and embodiments may be devised by those skilled in the art.

The invention claimed is:

1. A device for stabilizing a first vertebra relative to a second vertebra, the device comprising:
    a superior endplate having an inferior surface and a motion limiting member, said motion limiting member extending downward below said inferior surface, and a superior screw anchor member extending upward from the superior endplate;
    an inferior endplate having a superior surface and a motion limiting member, said motion limiting member extending upward above said superior surface, and an inferior screw anchor member extending downward from the inferior endplate;
    a compressible and flexible body having a superior surface and an inferior surface, said superior surface of said body facing said inferior surface of said superior endplate, said inferior surface of said body facing said superior surface of said inferior endplate, said body being held in contact with and laterally between said superior endplate and said inferior endplate by said motion limiting members; and
    a locking plate including a horizontal plate, a superior screw anchoring member that extends upwardly from the horizontal plate, a first void region adjacent the superior screw anchoring member and above the horizontal plate, an inferior screw anchoring member that extends downwardly from the horizontal plate, and a second void region adjacent the inferior screw anchoring member and below the horizontal plate, wherein the locking plate is configured to overlie the superior endplate and the inferior endplate such that the first void region overlies the superior screw anchoring member of the superior endplate and the second void region overlies the inferior screw anchoring member of the inferior endplate,
    wherein the superior screw anchoring member of the locking plate and the inferior screw anchoring member of the locking plate are laterally offset.

2. The device according to claim 1, wherein said motion limiting member on said superior endplate and said motion limiting member on said inferior endplate are staggered with regard to each other.

3. The device according to claim 1, wherein:
    said body has a height; and
    said motion limiting member on said superior endplate is shorter than said height of said body.

4. The device according to claim 1, wherein:
    said body has a side; and
    said motion limiting member on said superior endplate and said motion limiting member on said inferior endplate both support said body along said side.

5. The device according to claim 1, wherein:
    said body has a first side and a second side opposing said first side;
    said motion limiting member disposed on said superior endplate supports said body along said first side of said body; and
    said motion limiting member disposed on said inferior endplate supports said body along said second side of said body.

6. The device according to claim 5, further comprising a further motion limiting member disposed on said superior endplate, said further motion limiting member supporting said body along said second side of said body.

7. The device according to claim 1, wherein at least one of said endplates is shaped substantially like a quadrilateral.

8. The device according to claim 1, wherein at least one of said endplates complements a contact surface of a body of a vertebra to be supported by said at least one of said endplates.

9. The device according to claim 1, wherein at least one of said endplates has bone growth bore formed therein.

10. The device according to claim 1, wherein said superior screw anchoring member is configured to be fastened to the first vertebra.

11. The device according to claim 10, wherein said inferior screw anchoring member is configured to be fastened to the second vertebra.

12. The device according to claim 11, further comprising a fastener connected to said inferior screw anchoring member of the inferior endplate, said fastener being configured to secure said inferior screw anchoring member to the second vertebra.

13. The device according to claim 10, further comprising a fastener connected to said superior screw anchoring member of the superior endplate, said fastener being configured to secure said superior screw anchoring member to the first vertebra.

14. A device for stabilizing a first vertebra relative to a second vertebra, the device comprising:

a superior endplate having an inferior surface and a motion limiting member, said motion limiting member extending downward below said inferior surface;

an inferior endplate having a superior surface and a motion limiting member, said motion limiting member extending upward above said superior surface, and an inferior screw anchor member extending downward from the inferior endplate;

a compressible and flexible body having a superior surface and an inferior surface, said superior surface of said body facing said inferior surface of said superior endplate, said inferior surface of said body facing said superior surface of said inferior endplate, said body being held in contact with and laterally between said superior endplate and said inferior endplate by said motion limiting members; and a locking plate including a horizontal plate, a superior screw anchoring member that extends upwardly from the horizontal plate, a first void region adjacent the superior screw anchoring member and above the horizontal plate, an inferior screw anchoring member that extends downwardly from the horizontal plate, and a second void region adjacent the inferior screw anchoring member and below the horizontal plate, wherein the locking plate is configured to overlie the superior endplate and the inferior endplate such that the second void region overlies the inferior screw anchoring member of the inferior endplate wherein the superior screw anchoring member of the locking plate and the inferior screw anchoring member of the locking plate are laterally offset, and wherein the superior screw anchoring member of the locking plate is vertically aligned above the motion limiting member of the inferior endplate.

15. The device according to claim 14, wherein said motion limiting member on said superior endplate and said motion limiting member on said inferior endplate are staggered with regard to each other.

16. The device according to claim 14, wherein:
said body has a height; and
said motion limiting member on said superior endplate is shorter than said height of said body.

17. The device according to claim 14, wherein:
said body has a side; and
said motion limiting member on said superior endplate and said motion limiting member on said inferior endplate both support said body along said side.

18. The device according to claim 14, wherein:
said body has a first side and a second side opposing said first side;
said motion limiting member disposed on said superior endplate supports said body along said first side of said body; and
said motion limiting member disposed on said inferior endplate supports said body along said second side of said body.

19. A device for stabilizing a first vertebra relative to a second vertebra following a discectomy or a corpectomy, the device comprising:

a superior endplate having an anterior edge, a posterior edge, a right edge, a left edge, an inferior surface, a textured superior surface, and motion limiting members extending inferiorly from said inferior surface, said superior endplate having a bone growth bore formed therein;

an inferior endplate having an anterior edge, a posterior edge, a right edge, a left edge, a superior surface, a textured inferior surface, and motion limiting members, one of said motion limiting members extending superiorly said inferior endplate having a bone growth bore formed therein;

a compressible and flexible body having a superior surface, an inferior surface, and a height defined between said superior surface and said inferior surface, said superior surface of said body facing said inferior surface of said superior endplate, said inferior surface of said body facing said superior surface of said inferior endplate, said body being held in contact and laterally between said superior endplate and said inferior endplate by said motion limiting members;

a superior screw anchoring member extending superiorly from said anterior edge of said superior endplate, said superior screw anchoring member being configured to connect to a superior vertebra;

an inferior screw anchoring member extending inferiorly from said anterior face of said inferior endplate, said inferior screw anchoring member being staggered from said superior screw anchor and configured to connect to an inferior vertebra; and wherein the device further comprises a locking plate including a horizontal plate, a superior screw anchoring member that extends upwardly from the horizontal plate, a first void region adjacent the superior screw anchoring member and above the horizontal plate, an inferior screw anchoring member that extends downwardly from the horizontal plate, and a second void region adjacent the inferior screw anchoring member and below the horizontal plate, wherein the locking plate is configured to overlie the superior endplate and the inferior endplate such that the first void region overlies the superior screw anchoring member of the superior endplate and the second void region overlies the inferior screw anchoring member of the inferior endplate, wherein the superior screw anchoring member of the locking plate and the inferior screw anchoring member of the locking plate are laterally offset, wherein the superior screw anchoring member of the locking plate is vertically aligned above the motion limiting member of the inferior endplate.

* * * * *